(12) United States Patent
Stoop et al.

(10) Patent No.: US 6,256,537 B1
(45) Date of Patent: Jul. 3, 2001

(54) PACEMAKER SYSTEM WITH INHIBITION OF AV NODE FOR RATE REGULATION DURING ATRIAL FIBRILLATION

(75) Inventors: Gustaaf A. P. Stoop, Dieren; Josephus P. A. Smit, Enschede; Peter Van Dam, Nijmegen, all of (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/270,796

(22) Filed: Mar. 17, 1999

(51) Int. Cl.[7] .................................................. A61N 1/362
(52) U.S. Cl. ................................................................ 607/14
(58) Field of Search ................................... 607/4, 5, 9, 14

(56) References Cited

U.S. PATENT DOCUMENTS

| | | | |
|---|---|---|---|
| 5,320,642 | * 6/1994 | Scherlag | 607/9 |
| 5,480,413 | 1/1996 | Greenhut et al. | |
| 5,792,193 | 8/1998 | Stoop | |
| 5,876,422 | 3/1999 | van Groeningen | |
| 5,916,239 | * 6/1999 | Geddes et al. | 607/14 |

OTHER PUBLICATIONS

Prystowsky, Eric N., "Subthreshold Conditioning Stimuli Inhibit Human Atrial and Ventricular Myocardium," Chapter 3, *Prevention of Tachyarrhythmias With Cardiac Pacing*, Futura Publishing Company, 1997.

Scaglione, Jorge, et al., "Reversion of Atrial Fibrillation in Dogs By Rapid Infusion of Cold Saline Solution," NASPE Abstracts, *Pace*, vol. 16, Apr. 1993, Part II.

Wittkampf, Frederik, et al., "Rate Stabilization by Right Ventricular Pacing in Patients with Atrial Fibrillation," *Pace*, vol 9, Nov–Dec. 1986, Part II, pp. 1147–53.

Wittkampf, Frederik, et al., "Effects of Right Ventricular Pacing on Ventricular Rhythm during Atrial Fibrillation," *JACC*, vol. 11, Mar. 1988, pp. 539–45.

Lau, Chu–Pak, et al., "A New Pacing Method for Rapid Regularization and Rate Control in Atrial Fibrillation" *American Journal of Cardiology*, vol. 65, May 15, 1990, pp. 1198–1203.

* cited by examiner

*Primary Examiner*—George R. Evanisko
(74) *Attorney, Agent, or Firm*—Thomas F. Woods; Michael J. Jaro; Harold Patton

(57) ABSTRACT

There is provided a system for regulating ventricular rate in the presence of abnormally high atrial rates, e.g., during episodes of atrial fibrillation. During such an episode, the system, preferably incorporated into an implantable pacemaker, applies subthreshold bursts of stimulus pulses to or proximate to the patient's AV node so as to inhibit conduction of electrical signals through to the ventricle during the bursts. The bursts are timed in relation to the last conducted ventricular signal, and in terms of burst length, to provide a rate of conducted signals through the AV node which results in a substantially regular and reduced ventricular rate. During the inhibition mode of operation, the system monitors to determine the efficacy of inhibition, by tracking the percentage of ventricular senses that occur during the burst periods. When inhibition is found to be below an acceptable percentage, the system carries out an inhibition test and re-adjusts the burst parameters to provide bursts of optimized stimulation energy.

15 Claims, 9 Drawing Sheets

PACEMAKER SYSTEM WITH INHIBITION OF AV NODE FOR RATE REGULATION DURING ATRIAL FIBRILLATION

FIELD OF THE INVENTION

This invention relates to cardiac pacing systems with the capability of responding to episodes of atrial fibrillation and other atrial arrhythmias and, in particular, implantable pacing systems which respond to such an episode by controllably inhibiting conduction of at least some of the atrial signals to the ventricle until the episode terminates naturally.

BACKGROUND OF THE INVENTION

Modern cardiac pacing systems have incorporated substantial capability for detecting and dealing with various arrhythmias. Of particular importance are atrial arrhythmias such as atrial fibrillation (AF), which may lead to serious complications. Atrial fibrillation is manifested as an irregular disorganized activity of the heart, and in the absence of complete AV block, the ventricular response is irregular and random. The irregularity of the resulting cardiac rhythm adversely affects the contractile performance of the heart. It is a source of considerable morbidity and mortality; AF is the leading cause of embolic stroke. As used hereinafter, the term atrial fibrillation, or AF, refers broadly to the class of dangerous atrial arrhythmias, during episodes of which it is desired to inhibit conduction of most of the atrial signals to the ventricles. Pacemakers have attempted to deal with such arrhythmias by simply switching into an asynchronous mode, such that ventricular pacing does not try to track the dangerous atrial excitations. However, with ordinary asynchronous ventricular pacing and continued conduction of the atrial signals through the AV node, a certain percentage of the atrial signals will get through to the ventricle and thus cause chaotic spontaneous ventricular contractions and paced contractions, resulting in an undesirable cardiac condition. Patients with paroxysmal or chronic AF and intact AV conduction who are highly symptomatic and drug refractory are presently candidates for His ablation. This is, of course, a procedure which stops conduction of all atrial signals to the ventricle permanently. The result is that the ventricle needs to be paced permanently even though the atrium contracts normally most of the time.

Another technique that is in use is that of delivering a cardioversion shock to the patient's heart. This can be done during general anesthesia, which of course is impractical for a patient who has repeated and rather long-occurring episodes. Such a patient would also be a candidate for an implantable cardioverter device. However, such devices are very expensive, and the shocks are not welcome to the patient, i.e., they may be painful. Further, if the episodes occur too frequently, these devices have a limited lifetime due to the energy expenditure of each shock.

Another approach known in the literature is to cool the atrium, thereby slowing conduction in the atrial tissue to the point of terminating the atrial fibrillation. See Abstract, Scaglione et al, PACE, Vol. 16, p 880, April 1993, Part II. In this approach, the entire atrium is cooled by introduction of a bolus of cold saline solution. See also U.S. Pat. No. 5,876,422, issued Mar. 2, 1999, showing a system for Peltier cooling of the AV node during which the ventricle must be paced asynchronously for the duration of the AF episode.

Another approach to the problem is for the pacemaker to respond by aggressively pacing at a higher, but more stable rate. See, for example, U.S. Pat. No. 5,480,413. See also U.S. Pat. No. 5,792,193, which smooths the ventricular rate by an algorithm that allows some spontaneous ventricular contractions, and delivers some pace pulses which overdrive the spontaneous rate.

However, there remains a substantial need for an improved system and technique for effectively regulating the ventricular rate until the atrium can return on its own to a normal sinus rhythm, and without requiring a high ventricular rate so that the ventricle be paced asynchronously.

SUMMARY OF THE INVENTION

It is an object of this invention to provide a stimulating system, preferably an implantable system such as a pacemaker system, which is responsive to atrial fibrillation by regulating the rate of atrial signals which are conducted through the AV node, thereby regulating the rate of ventricular contractions. The invention is thus aimed at cardiac patients who have normal AV conduction but are susceptible to episodes of atrial fibrillation, and provides for limiting the ventricular rate by allowing passage of enough signals through to the ventricle to maintain at least a predetermined rate, and for inhibiting passage of other atrially generated excitation signals through the AV node. In this manner, the ventricle contracts synchronously with some of the atrial beats, but does not receive others, resulting in synchronous ventricular beats at a regulated rate.

The above object is achieved by responding to an episode of atrial fibrillation by generating and delivering subthreshold bursts of pulses to the patient's AV node, the bursts being controlled in energy level and frequency to inhibit conduction of signals through the node while they are being applied. Each burst is timed relative to a last sensed ventricular contraction so as to inhibit AV conduction for a period that is related to a desired V—V interval, or ventricular rate. The start of the burst, and the end of the burst are automatically adjusted to provide a desired burst duration; and the energy level of the burst is also automatically adjusted to ensure inhibition while minimizing energy expenditure. Inhibition threshold is tested by determining the percentage of ventricular contractions that occur at intervals shorter than that which corresponds to the predetermined regulation rate; when the percentage is too high, pulse level and/or frequency of pulses within the burst are adjusted to regain optimum inhibition. When the AF episode stops of its own accord, the system returns to a normal mode of pacing.

DESCRIPTION OF THE PREFERRED EMBODIMENTS

Figure 1A:
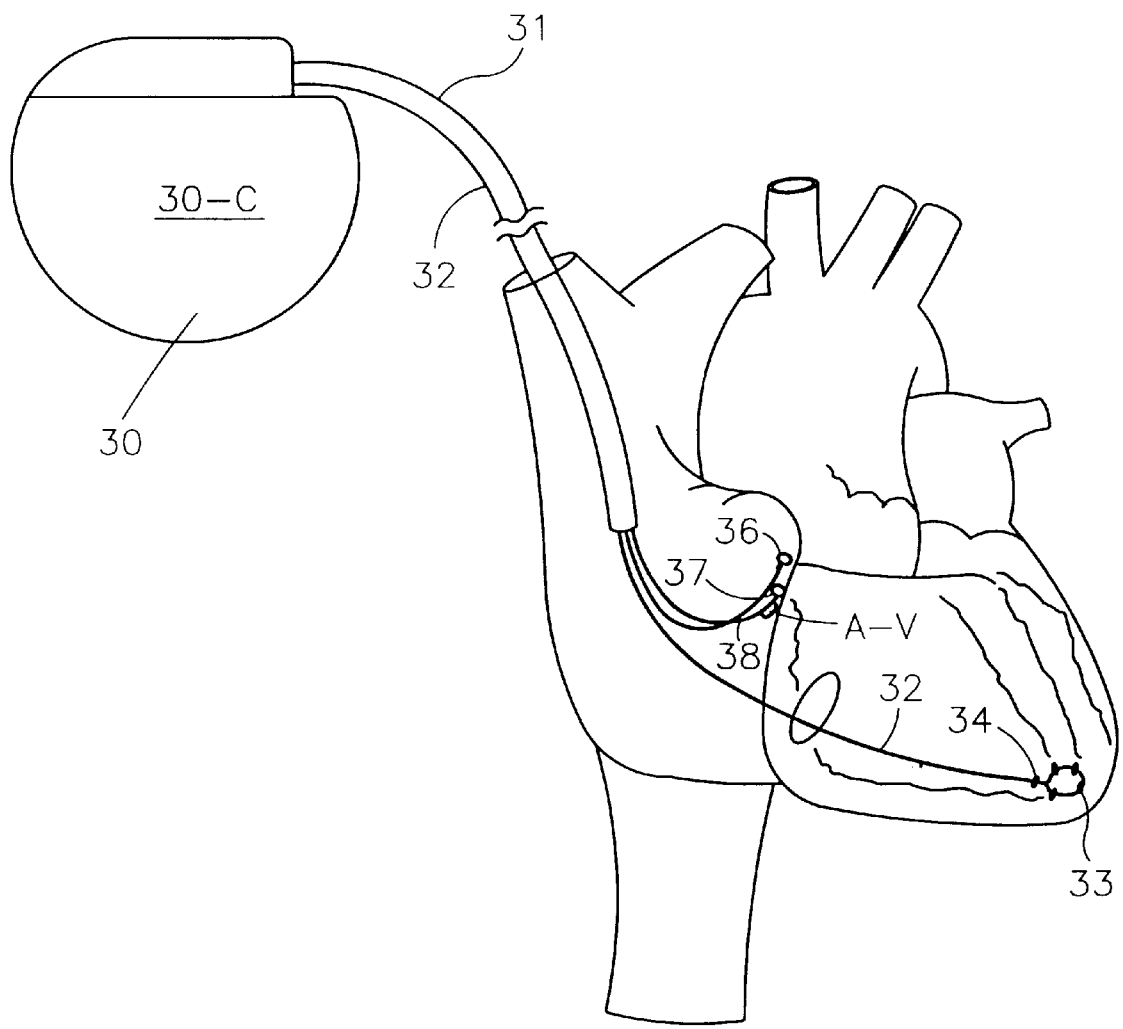
FIG. 1A is a schematic diagram of a pacemaker system in accordance with this invention, illustrating positioning of leads in the right atrium and the right ventricle, and also showing the positioning of at least one electrode for delivering bursts of inhibiting pulses proximate to the AV node.

Referring first to FIG. 1A, there is shown a diagram of a pacing system in accordance with this invention. Pacemaker 30 is suitably a dual chamber pacemaker, providing pacing pulses at least for delivery to the patient's ventricle, and preferably also providing for atrial pacing pulses. The pacemaker is encased in a pacemaker "can" 30-C, of conventional material. Ventricular pacing pulses are delivered from pacemaker 30 on lead 32, which is illustrated as being positioned with its distal end at about the apex of the right ventricle. Lead 32 may be unipolar or bipolar, and has at least one electrode, shown at 33, substantially at the distal tip, and may have a second ring electrode shown diagrammatically at 34. A second lead 31 is an atrial lead, for positioning against the inner wall of the atrium, as shown. This lead has a distal tip electrode 36, and suitably may also have a ring electrode 38 indicated as being displaced proximally from the distal end. It also carries at least one electrode 37, having a surface positioned for placement in proximity to the AV node, as indicated. Electrode 37 can be positioned on or proximate to the AV node, and the term "proximate" as used herein also refers to a position sufficiently close to the His, which enables inhibition of the excitation signal as it exits the AV node. It is important that the lead be fixed permanently proximate to the AV node, which can be done best by placing it in the triangle of Koch. It is known that in this area it is difficult to attach leads passively, and accordingly in the preferred embodiment a screw-in lead is used, as illustrated in FIG. 1C. Screwing a helical tip element into the AV node itself may or may not prove to be desirable; a safe procedure is for the physician to manipulate the separate atrial lead 31 into position so as to screw the tip end into the heart wall just proximate to the AV node or the His. As used hereinafter, reference to the AV node includes the exit area of the heart proximate to the AV node.

Figure 1B:
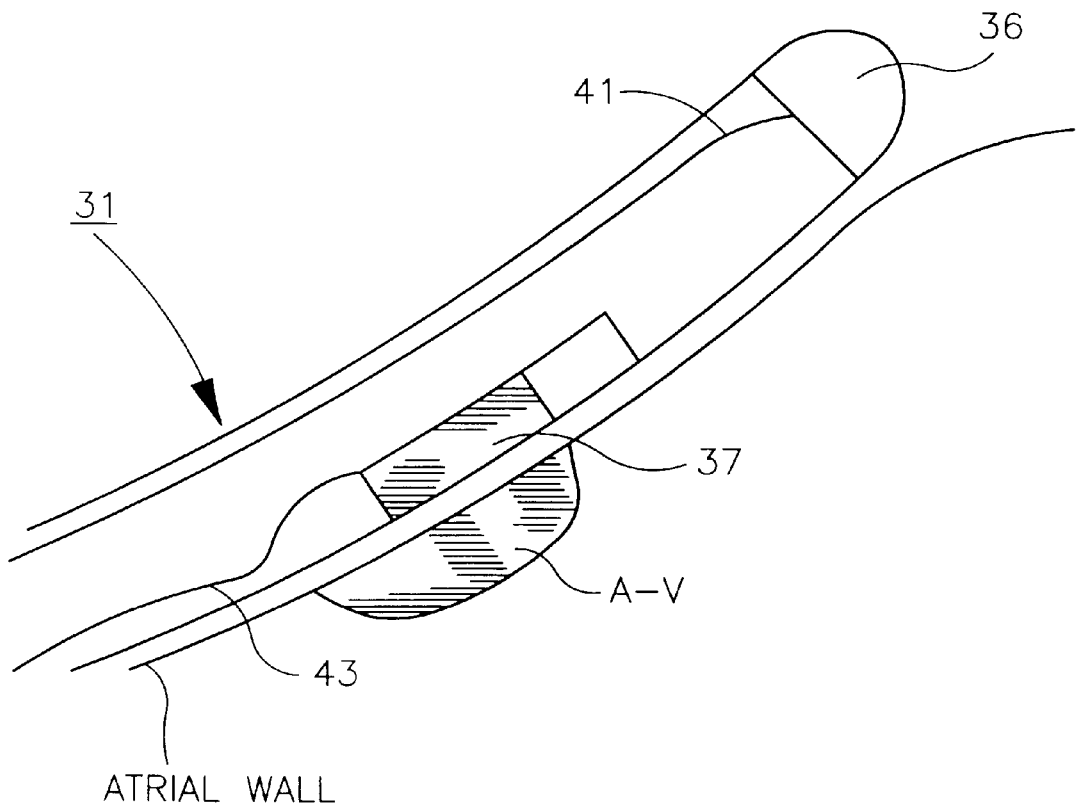
FIG. 1B is a detailed diagram of the distal end of an atrial lead in accordance with this invention.
Figure 1C:
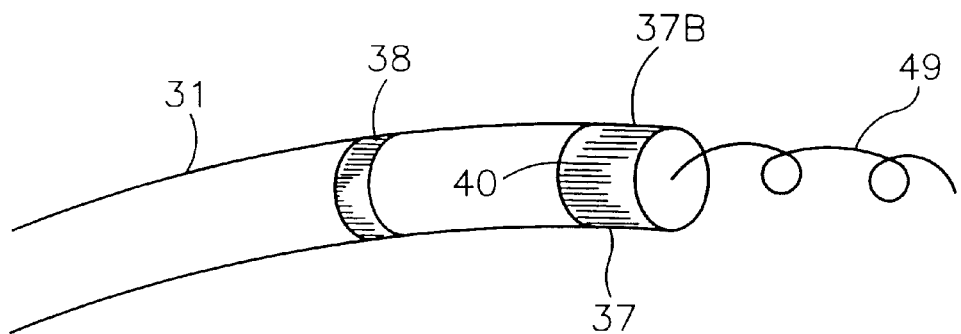
FIG. 1C is a detailed diagram of a preferred screw-in lead embodiment in accordance with this invention.

Referring now to FIG. 1B, there is shown a more detailed diagrammatic sketch of an atrial lead in accordance with this invention, carrying AV electrode 37. It is to be understood that FIG. 1B is illustrative only of electrode placement, and that the screw-in embodiment of FIG. 1C is presently a preferred embodiment. FIG. 1B shows details of the distal end of lead 31, which otherwise has a conventional outer casing and has a proximal end (not shown) for attachment to pacemaker 30 in a known manner. The AV electrode 37 is connected electrically to the pacemaker by conductor 43, and is positioned adjacent to distal end of the lead 31 so that it is in good contact with the AV node when the lead is fixed within the atrium. The burst may be delivered in unipolar fashion, i.e., between electrode 37 and the pacemaker can, or in a bipolar arrangement, in which case two AV ring electrodes are used. Also, as shown in FIG. 1B, conductor 41 connects to tip electrode 36, providing for delivery of pacing pulses from the pacemaker and delivery of sensed signals from the atrium back to the pacemaker, in a known fashion.

Referring to FIG. 1C, there is shown diagrammatically a preferred embodiment of lead 31, having a distally carried screw element 49 which can be pushed out from the distal tip for fixation into or around the AV node. The lead has a first ring electrode 37B at the tip end, and a second ring electrode 38 positioned about 10 mm proximal from the tip. Screw element 49 is held within the lead casing during introduction, and can be extended axially outward in a known manner; both ring electrodes and the screw element are connected by conductors to the pacemaker, or stimulator device. The physician may search the vicinity of the AV node to find the optimal position for fixating the lead in order to inhibit the AV node, at which time the screw is then pushed out and fixated. Stimulation can be performed with any desired combination of the 3 electrode elements. Additionally, for dual chamber pacemaker operation, any combination of one or more of the lead electrodes, as well as the pacemaker can, can be used for delivering pacing pulses and sensing atrial signals.

Figure 2:
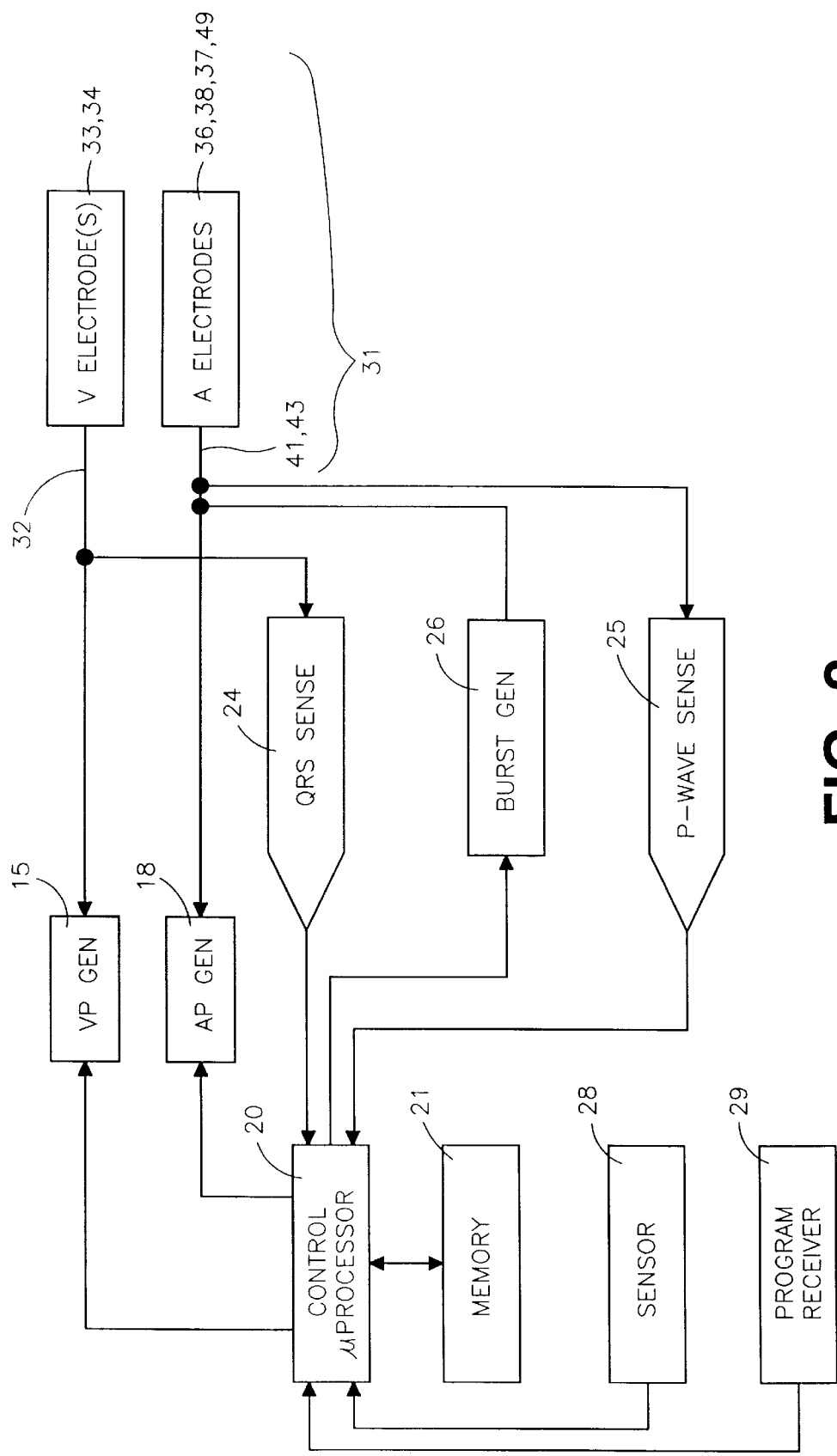
FIG. 2 is a block diagram of a pacemaker system in accordance with this invention, illustrating the primary functional blocks, including a burst generator for generating inhibiting bursts which are delivered proximate to the patient's AV node.

Referring now to FIG. 2, there is shown a block diagram of a pacemaker system in accordance with this invention. A generator 15 is provided for generating ventricular pace pulses, under control of control block 20. The ventricular pace pulses are delivered on lead 32 to one or more ventricular electrodes 33, 34. Likewise, generator 18 is provided for generating atrial pulses, which are delivered by lead 31 to atrial electrodes 37, 38 (or 49). Both generators 15 and 18 are controlled by control block 20, which preferably incorporates a microprocessor, for control of timing, amplitude, pulse width, etc. in a known manner. Memory 21 is interconnected with control block 20, for providing software for logic control, as well as pacing parameters and other data. Programmer receiver 29 is used to receive downloaded program data from an external programmer in a known fashion, and such received data is connected through control block 20 to storage in memory 21. A sensor 28 may be employed for obtaining one or more rate-indicating parameters, in a known manner.

Signals sensed from ventricular electrodes 33, 34 are connected through to QRS sense block 24, for appropriate signal processing and delivery to control block 20. Although not shown, the pacemaker may also sense T wave portions of the signals received from the ventricular electrodes. Likewise, signals from the atrial electrodes 37, 38, 49 are connected through to P wave sense block 25, for appropriate processing and connection through to control block 20.

Figure 3:
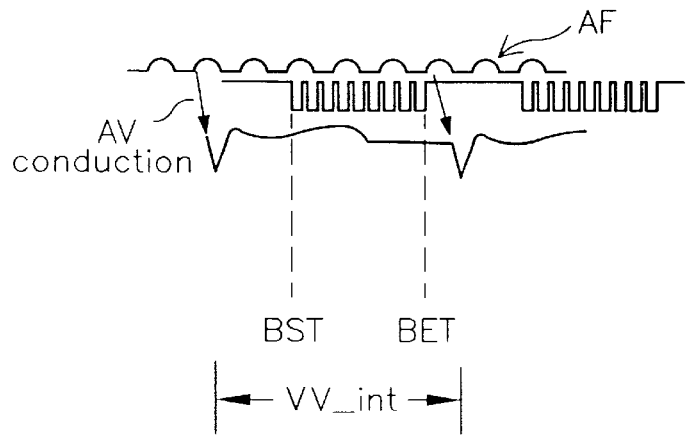
FIG. 3 is a timing diagram showing the timing of an inhibiting burst relative to a prior ventricular sense.

Of specific importance to the pacemaker system of this invention, burst generator 26 is controlled by block 20 to provide inhibiting bursts of subthreshold pulses to the AV node, in the event of an atrial arrhythmia. The bursts are delivered on conductor 43 to AV electrode 37 (or 49). The electrical parameters of the bursts, and the control of burst generation, are discussed in detail in connection with FIGS. 3–6B. Referring now to FIG. 3, there is shown a timing diagram illustrating the timing of an inhibiting burst relative to a ventricular sense (VS) and the ventricular refractory period. A burst is shown having a duration which extends from a start time (BST) to an end time (BET). The BST is timed to occur after an atrial signal is conducted through the AV node and produces a ventricular contraction, which is sensed (VS) by the device. Note that following a QRS there is a ventricular refractory interval, and BST is suitably timed to occur just before the end of this refractory period. As shown, after BET another atrial, or AF signal can be conducted through the AV node, producing a next VS. In this situation, the V—V interval is greater than the burst duration by the patient's natural AV interval plus the time from the prior VS to BST, showing that the patient ventricular rate can be controlled by controlling time of BST and BET, i.e., the burst duration and its timing relative to the last VS. This control can be achieved by adjusting the timing of both BST and BET.

If the monitored V—V interval is shorter than expected based on the burst duration and the AV delay, the BST may need adaptation; it may be that AF signals are slipping through between the end of the ventricular refractory period and BST. In a preferred embodiment, BST is caused to continually drift (e.g., in 10 microsecond steps) towards BET, in order to decrease the burst duration; but if BST is found to be too late it is set back with a much larger step (e.g., 10 ms). Drifting away from the VS stops when BST reaches a maximum programmable start time, and adaptation towards the VS stops at a programmable minimum. Alternately, BST can be set relative to the T wave, which is an indicator of the end of the ventricular refractory period. The value of BET depends on the desired ventricular interval, which may be programmed: by increasing the burst length, the AV node is inhibited longer, and ventricular rate is decreased. As is seen from the timing diagram, the first AF wave that is no longer inhibited is conducted to the ventricle with the AV delay. Assuming the atrial rate is very high compared to the V—V rate, BET is determined by the equation: BET=VV_int–AV_int, where BET is timed from the prior VS. The patient's AV_int can be determined, and thus BET can be set. Burst duration is then adjusted by adjusting BST, as is discussed further in connection with FIG. 5.

In a preferred embodiment, the available energy levels and frequencies of the burst pulses are programmable. Typical values are:

voltage-from 0.1 V to 5.0 V, in steps of 0.1V;
pulse width-from 0.1 ms to 10.0 ms, in steps of 0.1 ms;
current-from 0.5 mA to 5.0 mA, in steps of 0.1 mA; and
pulse interval-from 10 to 200 ms, in steps of 0.5 ms.

Figure 4A:
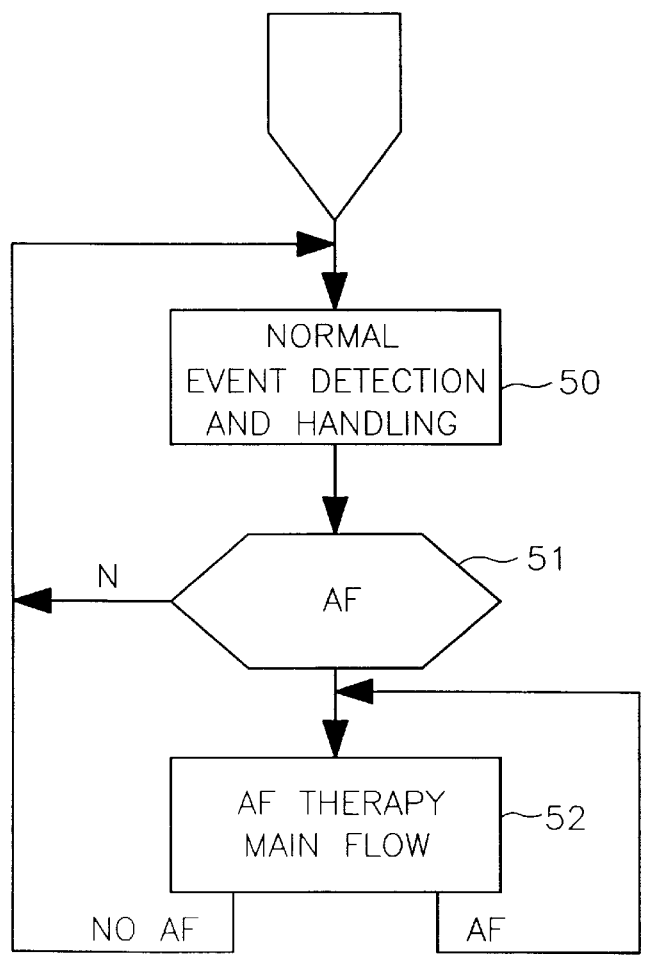
FIG. 4A is a flow diagram showing the relationship of the main AF therapy algorithm to the normal pacemaker routine.

Referring now to FIG. 4A, there is shown a simplified flow diagram showing the relationship of the AF therapy algorithm of this invention to the normal handling routine of a cardiac pacemaker. It is to be noted that the preferred environment of the invention is that of being incorporated into a pacemaker. However, it can likewise be used in other stimulating systems, e.g., as part of a pacemaker-cardioverter-defibrillator, or any other system dedicated to treatment of cardiac arrhythmias. In FIG. 4A, the normal pacemaker event detection and handling is illustrated at 50. Each cardiac cycle, the system tests for AF, as indicated at 51. Assuming no AF, the system remains in a conventional pacemaker mode. However if AF is detected, the system goes to the AF main flow 52, and regulates conduction of atrial signals to the ventricles. As long as AF continues, the system stays in this flow; if AF ceases, the system returns to the normal mode of operation.

Figure 4B:
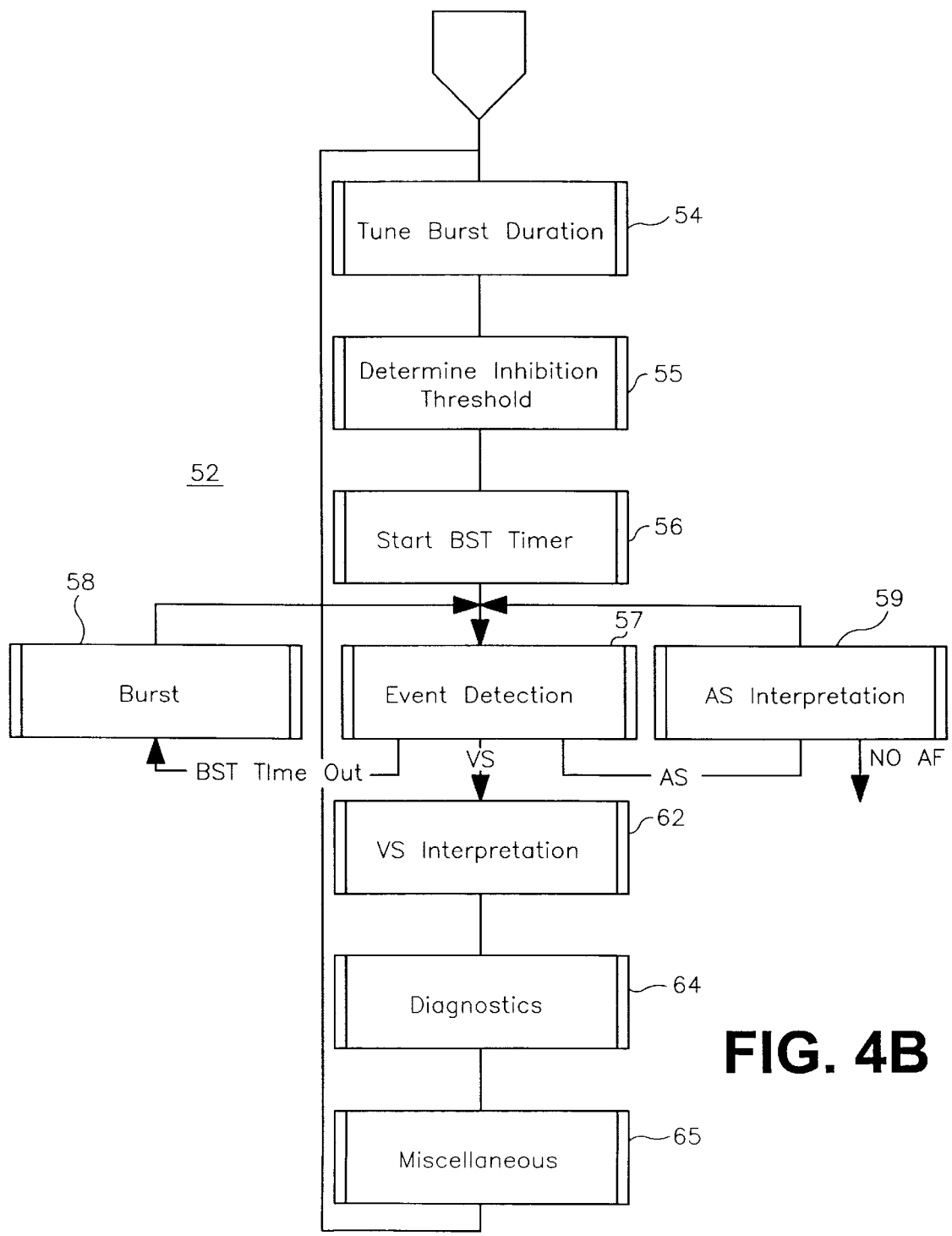
FIG. 4B is a flow diagram showing the main flow of the AF therapy algorithm of this invention.

Referring now to FIG. 4B, there is illustrated a flow diagram showing the primary routines carried out in the main flow 52. Starting at the top of the diagram, the Tune Burst Duration routine 54 is entered after a VS. This determines the start and end times of the burst with respect to the conducted VS. Next, at 55, the system carries out the Determine Inhibition Threshold routine. This controls the output pulse characteristics and frequency of the burst, to insure that AV conduction is inhibited during the burst. After this, at 56, the BST timer is started, to time out the start of the burst. BST may be timed out relative to the just sensed VS, or relative to the T wave, as discussed above. After this, the flow goes to the Event Detection routine, shown at 57. The next event can be time out of the BST timer; a VS; or an AS. The T wave may also be detected here, for use in setting the BST timer. If there is BST time out, the flow goes to routine 58, and controls generation and delivery of the burst from burst gen 26. After this, the next event is awaited at 57. When a VS occurs, it is interpreted at 62. Operations such as distinguishing ventricular extra systoles can be done here. The VV interval is saved. If the event detected at 57 is an atrial sense, it is interpreted at 59. The AA interval is saved, and it is determined whether AF has terminated. If there is no longer AF, the main flow is exited.

After VS interpretation at 62, the flow goes to a diagnostics block shown at 64. The diagnostics that are particularly important for this invention are those that indicate the efficacy of the therapy. For example, ventricular stability from beat to beat is important. The number of conducted ventricular senses (Vses) during the inhibition phase (i.e., conducted atrial signals during and despite the burst) is stored, preferably as a function of the burst output characteristics in histogram form. Also, test results when tuning and adjusting the burst can be stored. This data can be downloaded to a programmer for analysis by the physician, who then can re-program the burst control accordingly. Finally, at 65, various miscellaneous operations are performed, and the flow returns to block 54.

Figure 5:
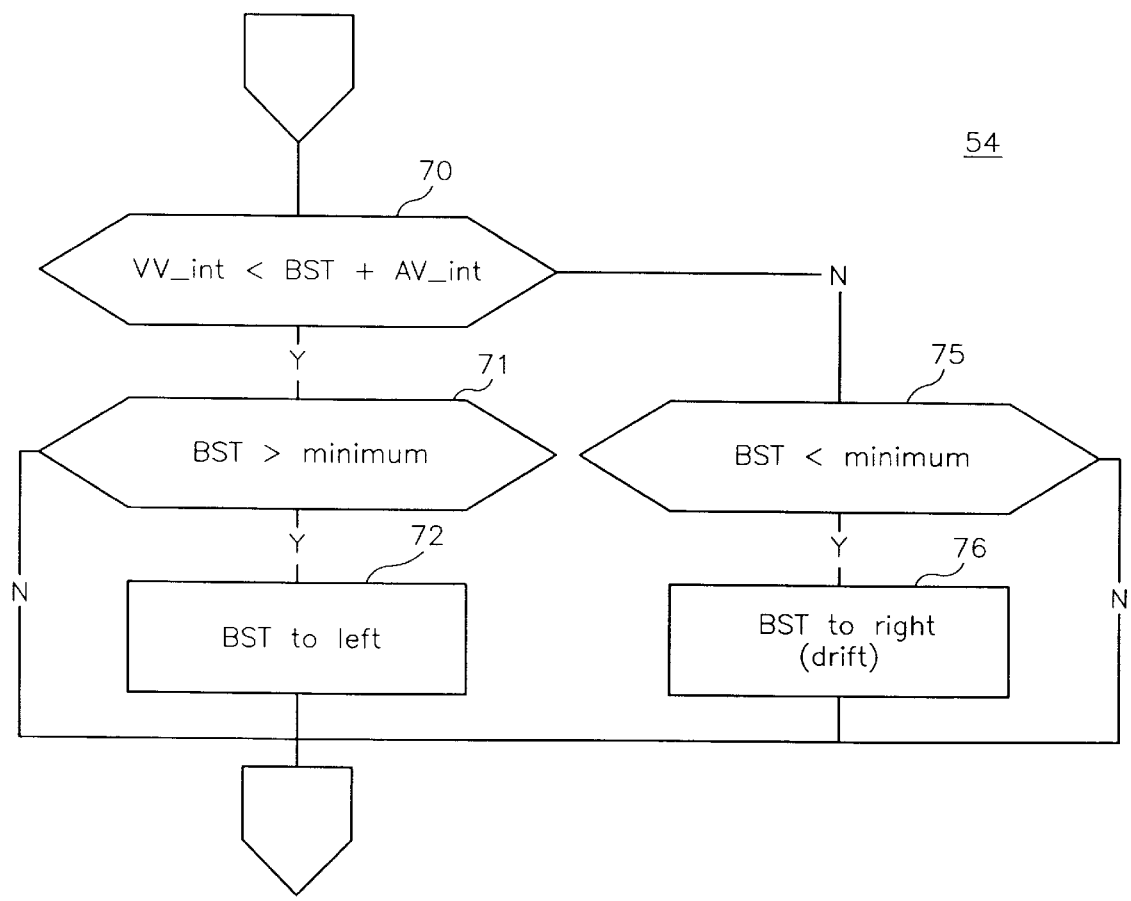
FIG. 5 is a flow diagram illustrating the determination of the burst duration.

Referring now to FIG. 5, there is shown a flow diagram for the tune burst duration routine 54. At 70, the VV_int is compared to BST+AV_int. If it is less, this means that an AF signal got started through the AV node before the burst was initiated at BST, such that BST needs to be shortened. At 71 it is determined whether BST is greater than the programmed minimum BST value. If no, this means that it is already at the minimum value, and the routine exits. If yes, at 72 BST is moved to the left (as seen in FIG. 3), or shortened, by a programmable decrement. Returning to block 70, if the answer is no, the routine goes to 75, and determines whether BST is less than the programmable maximum value. If no, meaning that it is already at the maximum, the routine exits; if yes, then at 76 BST is moved to the right (extended), i.e., BST drifts to minimize energy expenditure.

Figure 6A:
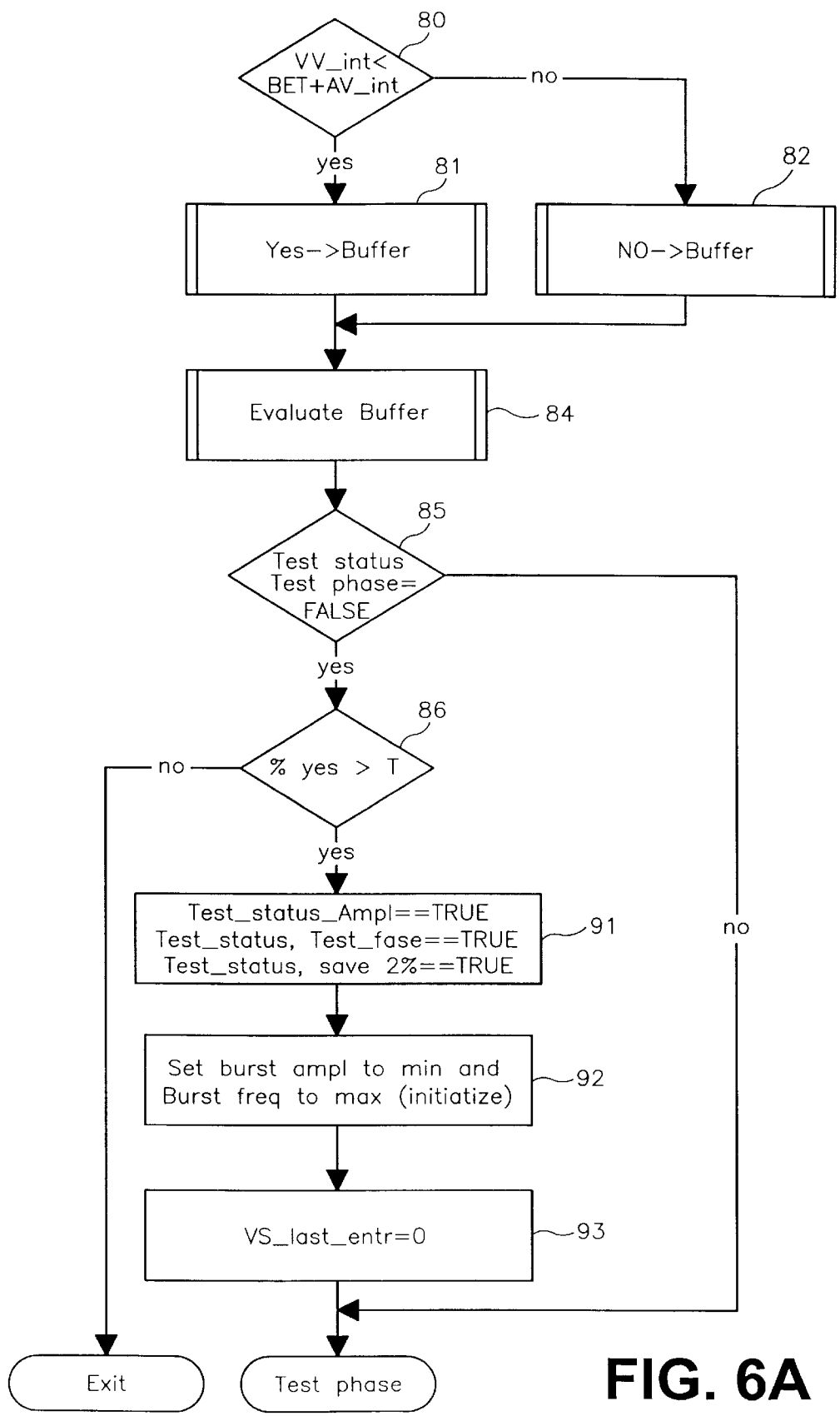
FIG. 6A is a flow diagram of a routine for determining when burst inhibition threshold should be tested.
Figure 6B:
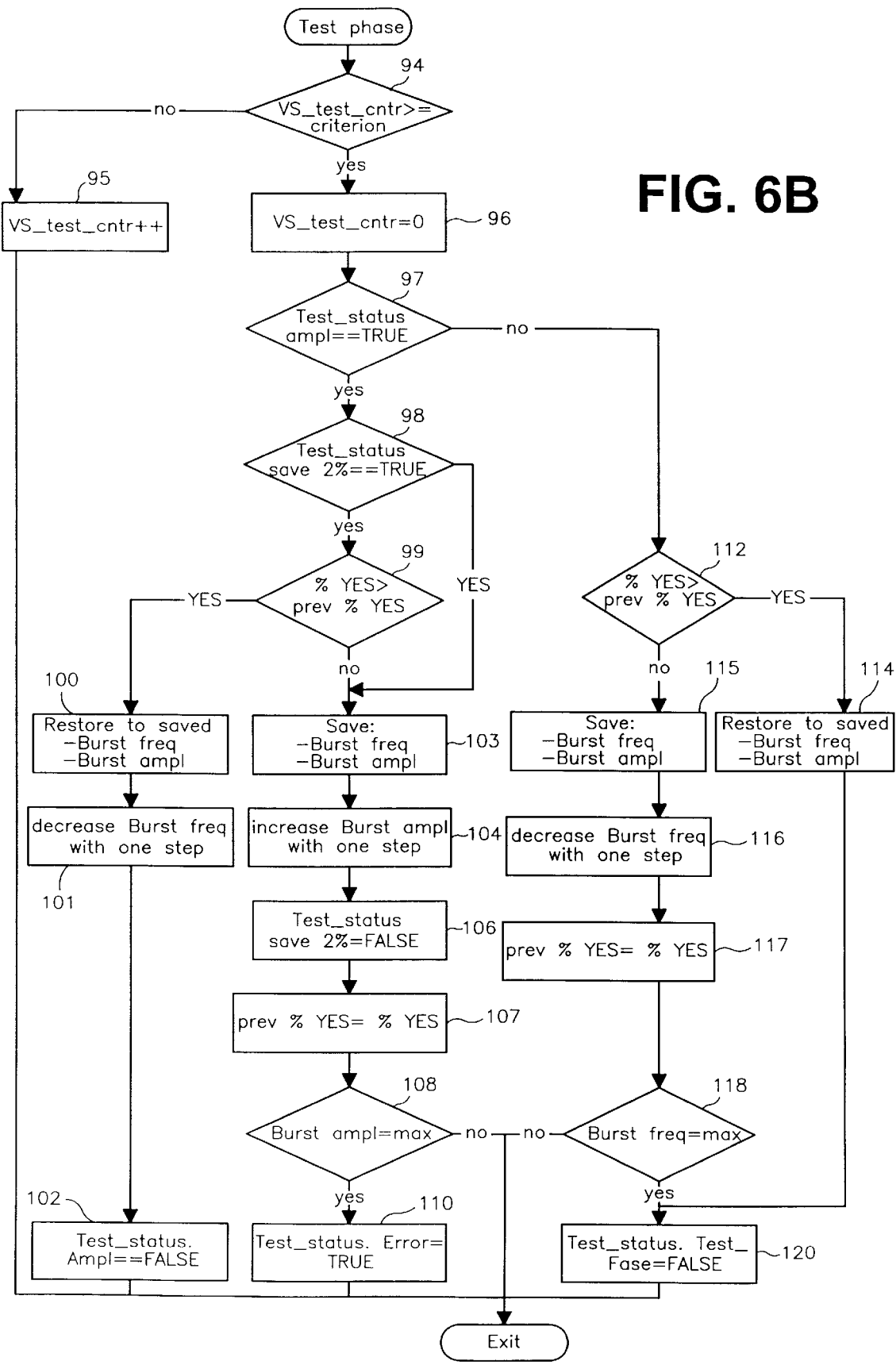
FIG. 6B is a flow diagram illustrating the test for determining inhibition energy level and frequency to provide optimum inhibition.

Referring now to FIG. 6A, there is shown a routine for determining when an inhibition threshold test should be undertaken, and for placing the pacemaker into a test phase. The object is to monitor the efficacy of the inhibition bursts, and if too many VS events are found, adjust the burst output level required to inhibit conduction through the AV node during the burst delivery. At 80, it is determined whether the latest VV_int was less than the value of BET+AV_int. If yes, this indicates that an atrial signal slipped through the AV node during the last burst. In this case, the routine goes to 81 and increments a YES counter, tallying the number of such failures to inhibit. If no, then the NO buffer is incremented, as shown at 82. At 84, the buffer is evaluated, e.g., the percentage of YES events is determined. At 85, the test status is determined, i.e., whether the test_phase flag is set FALSE. If no, the routine branches directly to the test phase, which is illustrated in FIG. 6B. However, if the test phase flag is FALSE, the routine goes to block 86 and determines whether the percentage of YES events is greater than a predetermined percentage T. If no, the routine exits. But if Yes, then the conclusion is that too many early VSs are occurring, i.e., the inhibition rate is unacceptably low, and threshold should be tested and the burst parameters reset.

The object of the test is to tune the burst output so as to achieve a reliably high inhibition efficacy rate, without raising output too greatly, which would result in wasted energy and possibly raising the pulse level above the AV node excitation threshold.

The pacemaker prepares for the test by setting certain flags, as seen at 91; the purpose of these flags is discussed in connection with FIG. 6B. At 92, the burst pulse amplitude is set to its lowest available level, and the burst pulse frequency to the highest value. A VS_test_counter is set to zero at 93, to enable counting of VS events. The pacemaker then goes to the test phase, illustrated in FIG. 6B.

At 94, the VS_test counter is compared with predetermined criteria, to see if enough VS events have taken place to test the burst parameters. If not, the routine goes to block 95 and increments the counter. When the count reaches the predetermined number, the counter is reset to zero at 96. At 97, it is determined whether the amplitude flag is set to TRUE. If yes, this means that the test is to proceed with adjustment of burst pulse amplitude. The routine goes to 98 where it checks to see if there is a reference percentage to compare to (save 2% means save percentage for the second test cycle). If yes, the routine branches to block 103; but if no, the routine goes to block 99 and determines whether the current % Yes is greater than the previously calculated %. If no, this means that amplitude is still below excitation threshold, and the pacemaker can try to raise it. At 103, the burst frequency and burst amplitude are saved, and then at 104 the burst amplitude is raised one step. At 106 the save 2% flag is set FALSE (meaning that there is no reference set), and at 107 the value of previous % is set equal to % Yes. At 108 the burst amplitude is compared to a programmed maximum value. If the amplitude has been raised to this max value, this means that maximum allowable amplitude has been reached without finding inhibition threshold, in which case the therapy must be stopped. The Error flag is set TRUE, and the routine exits. But, assuming that max amplitude has not been reached, the routine exits.

At the next pacemaker cycle, the pacemaker enters the routine of FIG. 6A at 80, and updates the % yes at 81. Since test phase is now TRUE, the pacemaker proceeds to the test phase of FIG. 6B, and runs another loop to determine if the increase in amplitude has raised % Yes greater than the previous % Yes (at 99). When the answer becomes yes, this means that amplitude has been raised too high; the bursts have an energy level above the AV node threshold, and are conducted through to the ventricle. The routine branches to block 100, and restores the previous burst frequency and burst amplitude (which had been saved at 103, before amplitude was increased one step). Then, at 101 the burst frequency is decreased one step, to start the test of looking to see how much the burst energy can be reduced without making the burst energy too low to achieve inhibition. At 102, the Amplitude flag is set false, and the routine exits.

During the next cycles, the required number of VS events are collected, until the VS_test counter reaches the required number at 94. The test branches at 97, and goes to the right as seen in the flow, to test for the desired frequency. At 112, the % Yes is compared to previous % Yes. Assuming it is not greater, at 115 the values of burst frequency and amplitude are saved, and at 116 frequency is decreased by one step. At 117, the value of prev % Yes is set equal to the current % Yes. At 118, the burst frequency is checked to see if it has been reduced to the minimum value. If yes, the frequency can not be lowered any more, so the test phase flag is set FALSE, and the routine exits. But if frequency remains above the programmed minimum value, the routine exits directly, and runs the test again at the decreased frequency. When the % Yes becomes greater than prev % Yes at 112, the routine branches to 114 and restores the burst parameters that had been previously saved at 115. Test phase or status is set FALSE at 120, and the test is over.

Figure 6C:
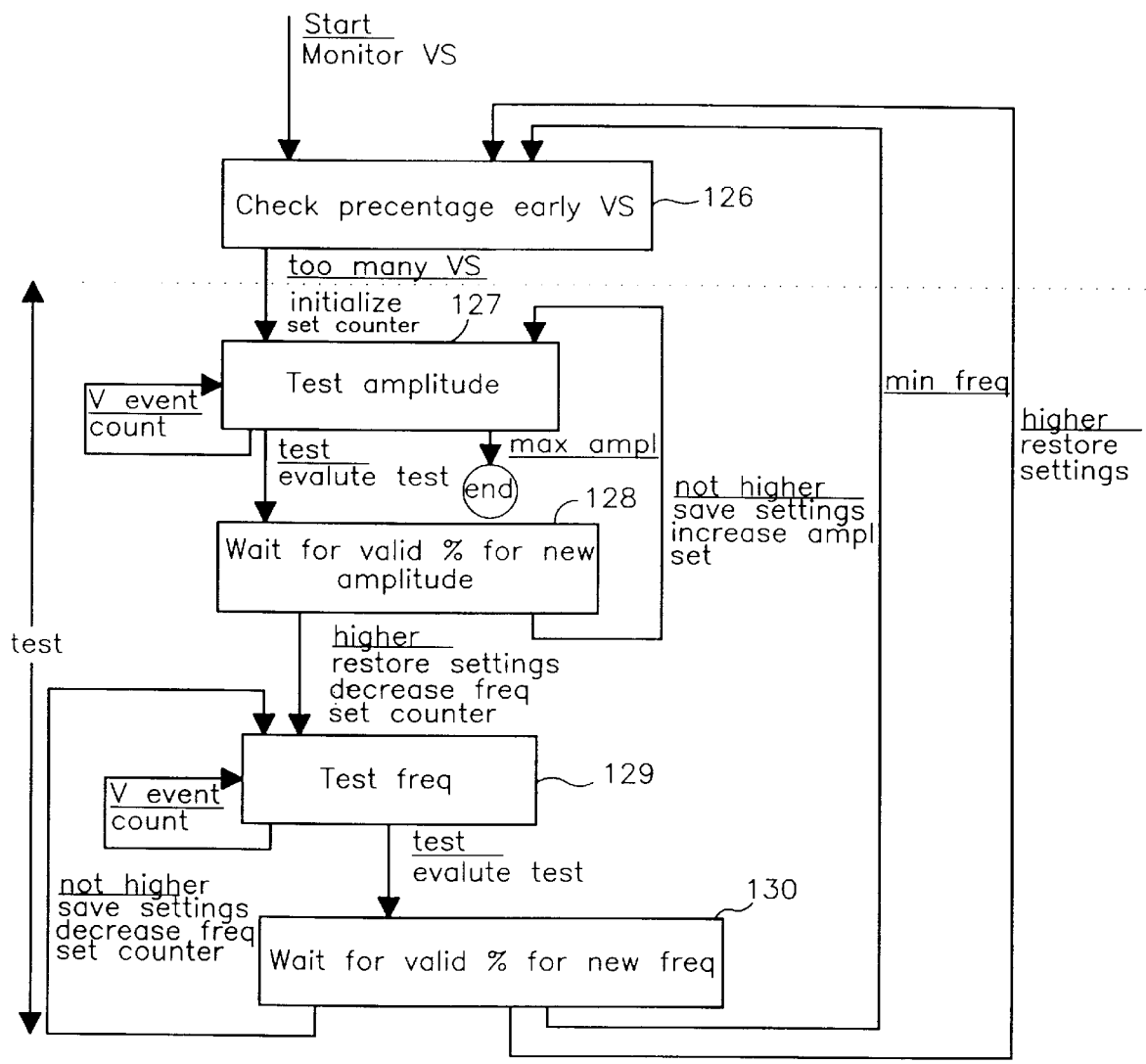
FIG. 6C is a state transition diagram for determining inhibition threshold, which further illustrates the test for setting the inhibition burst parameters.

Referring now to FIG. 6C, there is shown a state transition diagram which further illustrates the inventive feature of determining inhibition threshold. The disclosure of FIG. 6C augments that of FIGS. 6A and 6B. As seen, after monitoring of VS, the percentage of early VS events is determined at 126. If there are too many such VS events, the burst amplitude is tested at 127. When a valid higher percentage is determined at 128, the pacemaker then goes into a state of testing frequency, at 129. When the frequency test produces an increased percentage, the settings are restored, and the test is concluded.

There is thus disclosed a system and method for intermittently inhibiting the AV node by stimulating it with subthreshold bursts of pulses. The system monitors to determine whether the inhibition efficacy rate has decreased to an unacceptable level, and when this is found to be the case, an inhibition threshold test is carried out to readjust the pulse parameters so as to restore reliable inhibition. As seen, the pulses of the bursts can be adjusted in terms of both energy level and frequency. Although the invention has been illustrated by showing amplitude adjustment, it is to be understood that pulse width can also be adjusted. Further, while bursts of pulses are the preferred way of providing the inhibiting stimulation, other waveforms can be used in an equal manner. Thus, the term "burst" as used in claiming the invention embraces other waveforms than that used in illustrating the preferred embodiment, e.g., continuous and aperiodic waveforms.

What is claimed is:

1. An implantable stimulus system for providing atrial defibrillation therapy to a patient's heart, comprising:
   atrial sense means for sensing atrial signals from the patient's heart;
   burst means for generating bursts of pulses, each said burst having a controllable burst period;
   delivery means for delivering said bursts to the patients AV node; and
   inhibiting means for controlling an amplitude of each said burst to be subthreshold to said AV node so as to inhibit cardiac conduction through said AV node during each said burst period.

2. The system as described in claim 1, further comprising:
   ventricular sense means for sensing ventricular signals from the patient's heart;
   AF means for detecting an episode of atrial fibrillation;
   burst period means operative following a detection of an episode of atrial fibrillation, for determining said burst period; and
   burst control means for controlling said burst means to generate a said burst for a duration of said burst period following a sensed ventricular signal.

3. The system as described in claim 2, further comprising V—V means for providing a V—V interval for controlling the rate of ventricular contractions during said episode, and wherein said burst period means further comprises determining means for determining said burst period as a function of said V—V interval.

4. The system as described in claim 2, wherein said burst period means further comprises start means for determining a start time of said burst period following a sensed ventricular signal.

5. The system as described in claim 4, wherein said start means further comprises first timing means for timing out said burst start time in reference to a sensed ventricular signal.

6. The system as described in claim 5, wherein said first timing means further comprises means for determining a ventricular refractory period following a sensed ventricular signal and for setting said burst start time at about the end of said refractory period.

7. The system as described in claim 4, further comprising means for determining a time interval between sensed ventricular signals, and wherein said start means comprises adjust means for adjusting said start time in a direction to minimize said burst period when said time interval is less than the combination of said burst period plus a patient AV interval.

8. The system as described in claim 1, further comprising threshold means for determining the patient inhibition threshold, and wherein said inhibiting means comprises adjust means for adjusting the level of said burst pulses to maintain inhibition of the patient's AV node during each said burst.

9. The system as described in claim 8, further comprising ventricular sense means for sensing ventricular signals from the patient's heart and interval means for determining an interval of successive ventricular signals, and wherein said threshold means comprises VS means for determining when ventricular signals occur at VV intervals indicating that said bursts are not inhibiting conduction of ventricular signals through the patient's AV node.

10. The system as described in claim 9, wherein said VS means further comprises means for determining when a sensed ventricular signal has been conducted through the patient's AV node during delivery of a said burst.

11. The system as described in claim 10, further comprising percentage means for determining a measure of the percentage of sensed ventricular signals which have been conducted during a said burst, and response means for adjusting at least one parameter of said burst as a function of said measure.

12. The system as described in claim 11, wherein said response means further comprises means for adjusting the amplitude of said burst pulses.

13. The system as described in claim 12, wherein said response means further comprises means for adjusting a frequency of said burst pulses.

14. The system as described in claim 1, further comprising timing means for timing the generation of said bursts relative to sensed atrial signals so as to limit the rate Of said atrial signals that can pass through the patient's AV node to the patient's ventricle.

15. The system as described in claim 14, further comprising burst period means for controlling said burst period so that said rate is limited to a predetermined ventricular rate.

* * * * *

UNITED STATES PATENT AND TRADEMARK OFFICE
CERTIFICATE OF CORRECTION

PATENT NO.    : 6,256,537 B1
DATED         : July 3, 2001
INVENTOR(S)   : Stoop et al.

It is certified that error appears in the above-identified patent and that said Letters Patent is hereby corrected as shown below:

Column 10,
Line 20, change "Of" to -- of --.

Signed and Sealed this

Eighteenth Day of March, 2003

JAMES E. ROGAN
*Director of the United States Patent and Trademark Office*